(12) United States Patent
Park et al.

(10) Patent No.: US 9,964,749 B2
(45) Date of Patent: May 8, 2018

(54) TOTAL INTERNAL REFLECTION FLUORESCENCE MICROSCOPE (TIRFM)

(71) Applicant: INDUSTRY-ACADEMIC COOPERATION FOUNDATION, YONSEI UNIVERSITY, Seoul (KR)

(72) Inventors: No Cheol Park, Seoul (KR); Hyung Bae Moon, Seoul (KR); Won Sup Lee, Seoul (KR); Geon Lim, Seoul (KR); Guk Jong Choi, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days. days.

(21) Appl. No.: 15/339,091

(22) Filed: Oct. 31, 2016

(65) Prior Publication Data

US 2017/0153436 A1    Jun. 1, 2017

(30) Foreign Application Priority Data

Nov. 30, 2015   (KR) ......................... 10-2015-0168314

(51) Int. Cl.
*G02B 21/16*    (2006.01)
*G02B 21/08*    (2006.01)
(Continued)

(52) U.S. Cl.
CPC .......... *G02B 21/16* (2013.01); *G02B 21/082* (2013.01); *G02B 21/086* (2013.01); *G02B 21/33* (2013.01); *G02B 21/361* (2013.01)

(58) Field of Classification Search
CPC .... G02B 21/16; G02B 21/082; G02B 21/086; G02B 21/33; G02B 21/361
(Continued)

(56) References Cited

U.S. PATENT DOCUMENTS 9,719,928 B2 * 8/2017 Hell ................... G01N 21/6458
2002/0167724 A1 * 11/2002 Iketaki ............... G02B 21/0024
359/368

(Continued)

FOREIGN PATENT DOCUMENTS

JP         2004-271658 A      9/2004
KR    10-2012-0053235 A      5/2012
(Continued)

OTHER PUBLICATIONS

Stefan W. Hell et al., "Far-Field Optical Nanoscopy", Science, May 25, 2007, vol. 316, Issue 5828, pp. 1153-1158.*
(Continued)

*Primary Examiner* — Frank Font
(74) *Attorney, Agent, or Firm* — Sughrue Mion, PLLC

(57) ABSTRACT

Disclosed is a fluorescence microscope for imaging a specimen containing a fluorescent substance, the fluorescence microscope including an excitation light source configured to emit an excitation light that excites a fluorescent substance to emit fluorescence; a de-excitation light source configured to emit a de-excitation light that de-excites the fluorescent substance excited by the excitation light emitted from the excitation light source; an optical body configured to overlap a light emitted from the excitation light source and a light emitted from the de-excitation light source, and to discharge the overlapped light toward the specimen; and a solid immersion lens to which the light discharged from the optical body is incident, and configured to refract the light discharged from the optical body toward the specimen. A total internal reflection of the light incident to the solid immersion lens occurs on a bottom of the solid immersion lens.

20 Claims, 22 Drawing Sheets

(51) Int. Cl.
*G02B 21/36* (2006.01)
*G02B 21/33* (2006.01)

(58) Field of Classification Search
USPC .................................................. 359/385–390
See application file for complete search history.

(56) References Cited

U.S. PATENT DOCUMENTS

2007/0159690 A1\* 7/2007 Ulrich ................ G02B 21/0032
   359/385
2009/0219607 A1\* 9/2009 Saggau ............. G02B 21/0016
   359/305
2011/0002530 A1\* 1/2011 Zhuang ............. G01N 21/6428
   382/154
2016/0305883 A1\* 10/2016 Betzig .................... G02B 21/16

2016/0305884 A1\* 10/2016 Hell ................... G02B 21/0076

FOREIGN PATENT DOCUMENTS

KR  10-2012-0092223 A  10/2012
KR     10-1422618 B1   7/2014

OTHER PUBLICATIONS

Communication dated Jun. 29, 2017 from the Korean Intellectual Property Office in corresponding Korean Patent Application No. 10-2015-0168314.

Communication from the Korean Intellectual Property Office dated Dec. 20, 2016 in corresponding Korean Patent Application No. 10-2015-0168314.

\* cited by examiner

TOTAL INTERNAL REFLECTION FLUORESCENCE MICROSCOPE (TIRFM)

CROSS-REFERENCE TO RELATED APPLICATION

This application claims the priority benefit of Korean Patent Application No. 10-2015-0168314, filed on Nov. 30, 2015, in the Korean Intellectual Property Office, the disclosure of which is incorporated herein by reference.

BACKGROUND

1. Technical Field

At least one example embodiment relates to a total internal reflection fluorescence microscope (TIRFM), and more particularly, to a TIRFM that may cause a stimulated emission depletion (STED) phenomenon through a de-excitation light source to acquire a resolution beyond a diffraction limited feature in a horizontal direction and a vertical direction by including an aperture that allows a light emitted from an excitation light source for exciting a fluorescent substance and a light emitted from the de-excitation light source for de-exciting the fluorescent substance to be overlappingly incident to an object lens using a high refractive solid immersion lens (SIL) and adjusts an angle at which a total internal reflection occurs on the SIL due to the excitation light source.

2. Related Art

In the related art, an optical microscope has been used to image a specimen such as a bio-sample. However, an optical microscope as shown in FIG. 1A has an issue in that a resolution is relatively low in a vertical direction.

A total internal reflection fluorescence microscope (TIRFM) as shown in FIG. 1B is a microscope using an evanescent wave that occurs due to total internal reflection. The TIRFM refers to a fluorescent imaging scheme by an evanescent wave occurring due to total internal reflection by allowing a light to be incident to a contact interface between a high refractive index medium and a low refractive index medium at a threshold angle or more.

In general, the TIRFM uses an oil immersion lens. In this case, a transmission depth of the evanescent wave is 100 nm or less, which is significantly less than a transmission depth of a general optical system. Accordingly, the TIRFM may acquire a further high resolution in a vertical direction (hereinafter, also referred to as a vertical resolution).

In particular, since the TIRFM is the fluorescent imaging scheme by the evanescent wave, the TIRFM may be easily applicable to image the surface of a specimen. Accordingly, the TIRFM may be utilized to many researches, such as membrane dynamics, a single module imaging field, etc., using a relatively high vertical resolution and a surface imaging characteristic.

While the TIRFM may increase a vertical resolution, a resolution in a horizontal direction (hereinafter, also referred to as a horizontal resolution) may be limited by a diffraction limited feature. In particular, due to a characteristic of the oil immersion lens that a refraction index of an immersive material is limited, a numerical aperture (NA) of the lens is limited to 1.49. Thus, a horizontal resolution is slightly less than a vertical resolution.

Referring to FIGS. 2 and 3, a stimulated emission depletion (STED) microscopy that is one of ultra-high resolution technologies according to the related art relates to a scheme of overlappingly emitting two lights of different modes to a specimen to be observed. Once a fist light is emitted toward the specimen, energy is absorbed at the specimen and fluorescence is generated. Here, if a second light in a donut shape having a nanometer-sized empty center is emitted and overlaps the first light, the fluorescence is observed at the central space with the fluorescence being prohibited in a remaining area excluding the central space. A nanometer-unit image may be acquired by minutely moving the light and emitting the light toward the overall specimen in the above manner. If many images acquired as above are merged into a single image, a final image may be configured to have a resolution less than 0.2 μm.

SUMMARY

Example embodiments provide a total internal reflection fluorescence microscope (TIRFM) that may have a resolution much beyond an optical diffraction limited feature in a horizontal direction and a vertical direction by applying a solid immersion lens and stimulated emission depletion (STED) technology to a TIRFM.

According to an aspect of example embodiments, there is provided a total internal reflection fluorescence microscope (TIRFM) for imaging a specimen containing a fluorescent substance, the TIRFM including an excitation light source configured to emit an excitation light that excites the fluorescent substance to emit fluorescence; a de-excitation light source configured to emit a de-excitation light that de-excites the fluorescent substance excited by the excitation light emitted from the excitation light source; an optical body configured to overlap a light emitted from the excitation light source and a light emitted from the de-excitation light source, and to discharge the overlapped light toward the specimen; and a solid immersion lens to which the light discharged from the optical body is incident, and configured to refract the light discharged from the optical body toward the specimen. A total internal reflection of the light incident to the solid immersion lens occurs on a bottom of the solid immersion lens.

The TIRFM may further include an aperture configured to cover a portion of the excitation light emitted from the excitation light source.

The aperture may be configured to block a light of an area on which a total internal reflection does not occur on the bottom of the solid immersion lens in the excitation light incident to the solid immersion light by blocking a portion of the excitation light emitted from the excitation light source.

The aperture may be configured to block a light of an area corresponding to a threshold angle or less in the excitation light incident to the solid immersion light by blocking a portion of the excitation light emitted from the excitation light source.

The aperture may include a penetrator formed of a transparent material, and configured to allow the excitation light emitted from the excitation light source to pass; and a shield formed of an opaque material, and configured to block the excitation light discharged from the excitation light source. The penetrator and the shield may be provided so that an incidence angle of the excitation light incident to the solid immersion lens is greater than a threshold angle.

The shield may be provided in a circular shape to block a center of the excitation light emitted from the excitation light source, and the penetrator may be provided in a ring shape around the shield.

The TIRFM may further include a detector configured to detect a fluorescent light from the fluorescent substance of the specimen.

The optical body may include an excitation light transmitter configured to transfer the excitation light emitted from the excitation light source toward the specimen; and a de-excitation light transmitter configured to transfer the de-excitation light emitted from the de-excitation light source toward the specimen.

The excitation light transmitter and the de-excitation light transmitter may be dichroic mirrors or beam splitters configured to reflect the excitation light or the de-excitation light, and to allow a fluorescent light emitted from the fluorescent substance of the specimen to pass.

An object lens configured to allow the light discharged from the optical body to be incident toward the solid immersion lens may be provided below the optical body.

In response to the excitation light being incident to the solid immersion lens at an angle greater than a threshold angle, a total internal reflection may occur on the bottom of the solid immersion lens, an evanescent wave toward the specimen occurs on the solid immersion lens, and a fluorescent light of the fluorescent substance generated by the evanescent wave may be detected.

Pieces of the de-excitation light may be formed in a donut shape to overlap the excitation light on a neighboring area excluding a central area of the excitation light, and a horizontal resolution may increase in response to an occurrence of a simulated emission depletion (STED) phenomenon that de-excites the excitation light for exciting the fluorescent substance.

The solid immersion lens may be provided in a hemispherical shape, and the light discharged from the object lens may be incident to be vertical to the surface of the solid immersion lens and to increase a light collecting efficiency.

The TIRFM may further include a replicated lens configured to refract the light discharged from the optical body on the surface of the solid immersion lens or the object lens.

The bottom of the solid immersion lens may be provided in a conic shape that is upwardly inclined with getting closer from a center to an edge.

According to another aspect of example embodiments, there is provided a TIRFM for imaging a specimen containing a fluorescent substance, the TIRFM including an excitation light source configured to emit a first wavelength of an excitation light that excites the fluorescent substance; a de-excitation light source configured to emit a second wavelength of a de-excitation light that de-excites the fluorescent substance excited by the excitation light emitted from the excitation light source; an optical body configured to overlap a light emitted from the excitation light source and a light emitted from the de-excitation light source, and to discharge the overlapped light toward the specimen; a solid immersion lens to which the light discharged from the optical body is incident, and configured to refract the light discharged from the optical body toward the specimen; an aperture configured to adjust an amount of light emitted from the excitation light source by covering at least a portion of the excitation light source and to enable the light discharged from the optical body to cause a total internal reflection on a bottom of the solid immersion lens; and a detector configured to collect a fluorescent reaction of the fluorescent substance that has received the light discharged from the optical body.

The aperture may be configured to block a light of an area on which the total internal reflection does not occur on the bottom of the solid immersion lens in the excitation light incident to the solid immersion lens by blocking a portion of the excitation light emitted from the excitation light source.

The aperture may be configured to block a light of an area corresponding to a threshold angle or less in the excitation light incident to the solid immersion light by blocking a portion of the excitation light emitted from the excitation light source.

The aperture may include a penetrator formed of a transparent material, and configured to allow the excitation light emitted from the excitation light source to pass; and a shield formed of an opaque material, and configured to block the excitation light discharged from the excitation light source. The penetrator and the shield may be provided so that an incidence angle of the excitation light incident to the solid immersion lens is greater than a threshold angle.

The shield may be provided in a circular shape to block a center of the excitation light emitted from the excitation light source, and the penetrator may be provided in a ring shape around the shield.

According to at least some example embodiments, it is possible to acquire a horizontal and vertical resolution beyond a diffraction limited feature of a conventional optical microscope.

Also, an evanescent wave by total internal reflection occurs in a very thin area and the intensity thereof significantly decreases according to a progress distance. Accordingly, it is possible to locally observe a specimen dyed with a fluorescent substance and to observe a very thin portion, such as the surface of cell through a fluorescent reaction.

Also, since the evanescent wave has a significantly small thickness compared to a general TIRFM, it is possible to enhance an image contrast effect.

Also, since a numerical aperture (NA) is relatively high due to use of a solid immersion lens (SIL) compared to a conventional optical microscope, it is possible to acquire a relatively high resolution.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION OF THE INVENTION

Figure 1A:
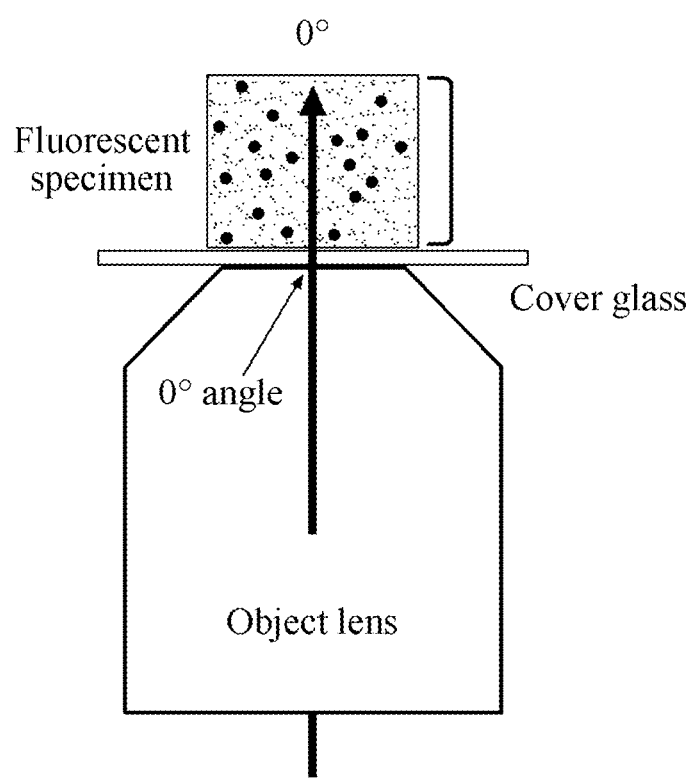
FIG. 1A illustrates a principle of acquiring an image of a specimen using an optical microscope according to a related art.
Figure 1B:
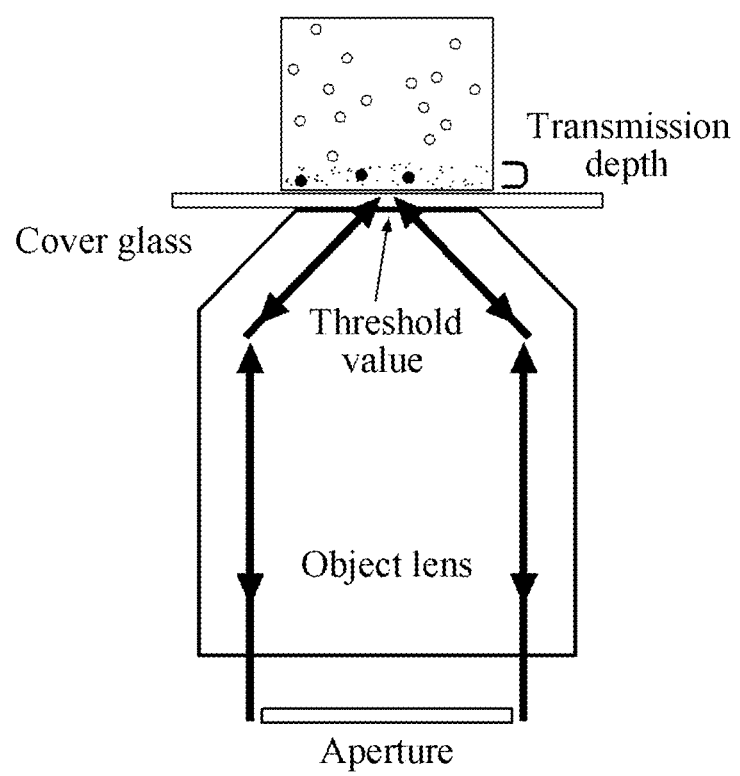
FIG. 1B illustrates a principle of acquiring an image of a specimen using a total internal reflection fluorescence microscope according to the related art.
Figure 2:
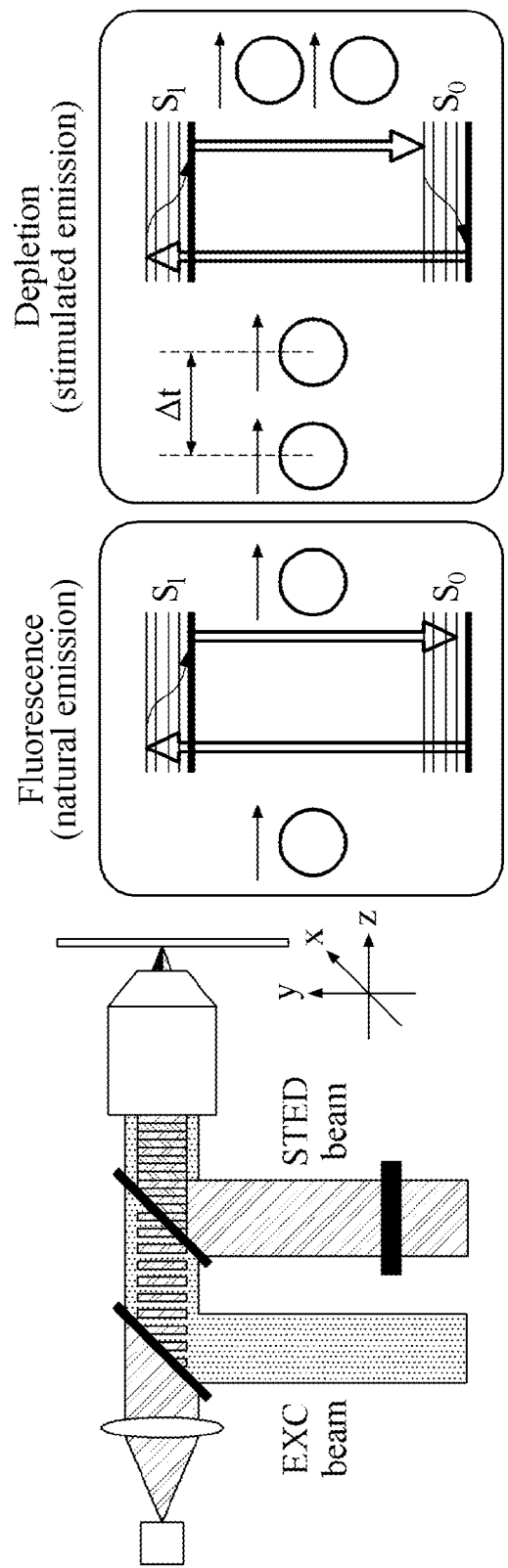
FIG. 2 illustrates a principle of acquiring an image of a specimen using an ultra-high resolution microscope based on a stimulated emission depletion (STED) phenomenon according to the related art.
Figure 3:
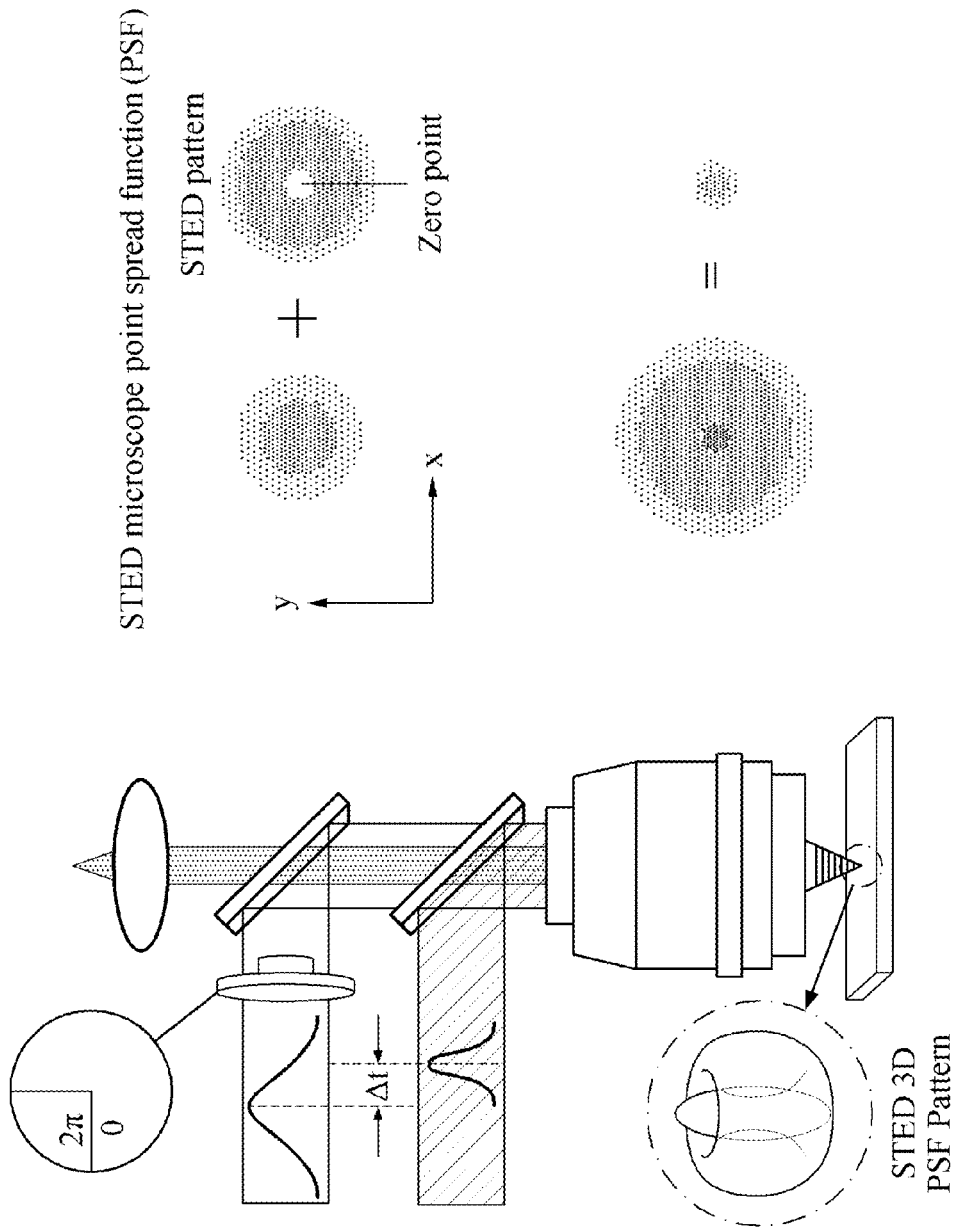
FIG. 3 illustrates a principle of overlapping two lights having different wavelengths using an ultra-high resolution microscope based on an STED phenomenon according to the related art.

Hereinafter, example embodiments will be described with reference to the accompanying drawings. Herein, thicknesses of lines, sizes of constituent elements, etc., illustrated in the drawings, may be exaggerated for clarity and convenience of description. Further, terms described in the following are ones defined based on functions in the present disclosure and thus, may vary based on the intent of a user or an operator, or custom. Accordingly, the definition of such terms should be made based on the overall description disclosed in the present specification.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

Hereinafter, example embodiments will be described with reference to the accompanying drawings. However, the present disclosure is not limited to the example embodiments and may be proposed to be different by adding, modifying, deleting, etc., constituent elements of the example embodiments, which still falls within the scope of the disclosure.

Figure 4:
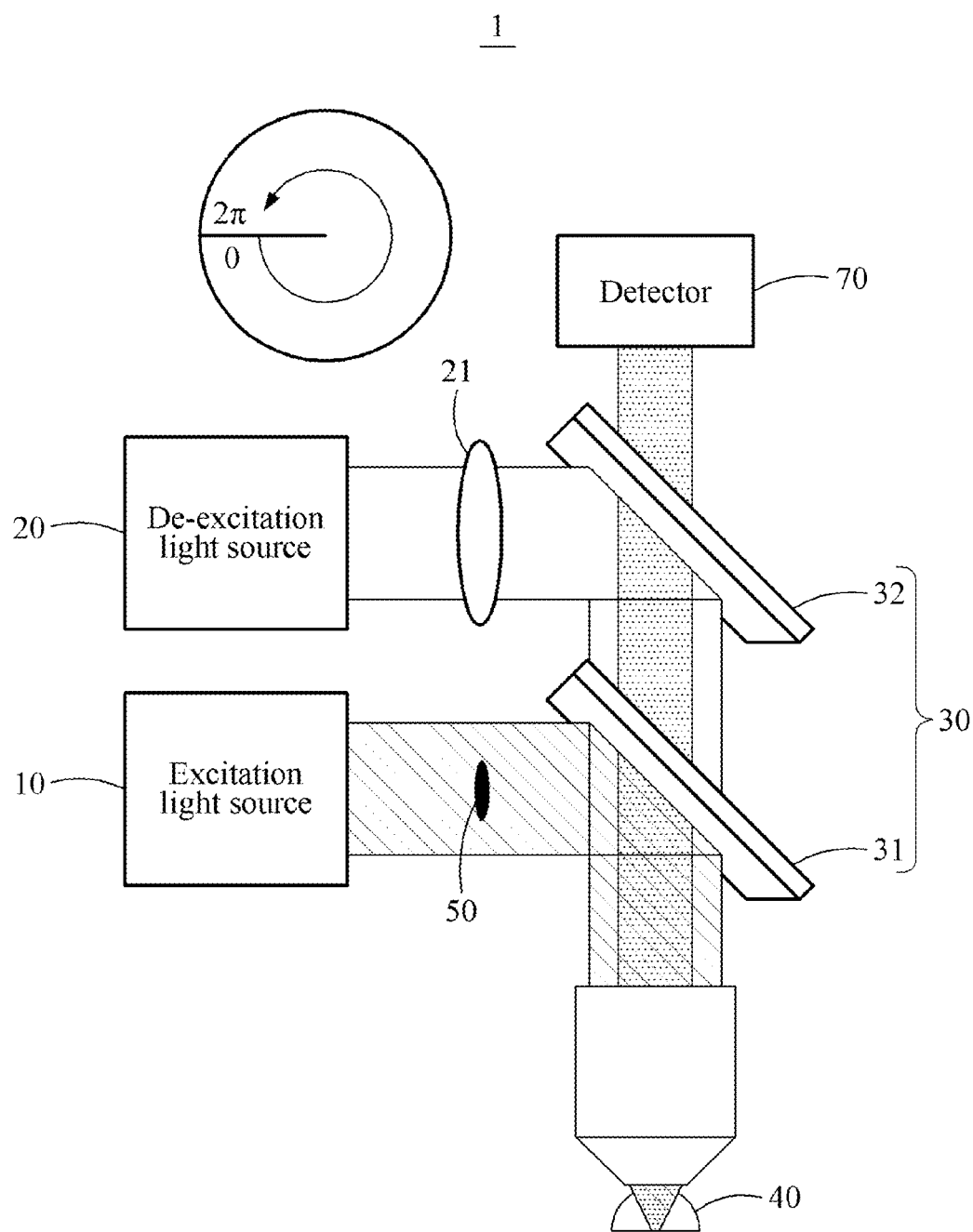
FIG. 4 illustrates an example of a fluorescence microscope according to at least one example embodiment.
Figure 5A:
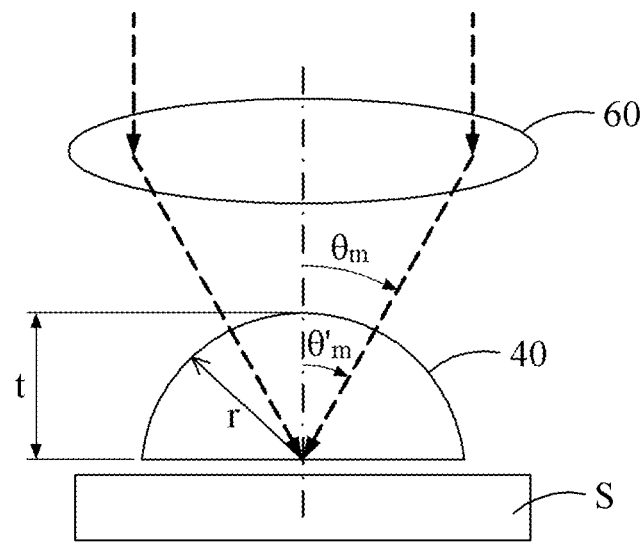
FIG. 5A illustrates an example of a path of excitation light incident from an object lens of a fluorescence microscope to a solid immersion lens (SIL) according to at least one example embodiment.
Figure 5B:
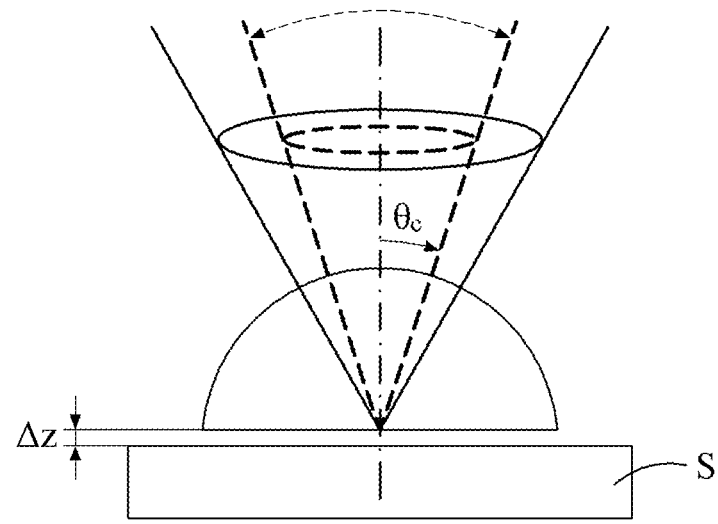
FIG. 5B illustrates an example of a threshold angle of excitation light incident to a SIL of a fluorescence microscope according to at least one example embodiment.
Figure 6A:
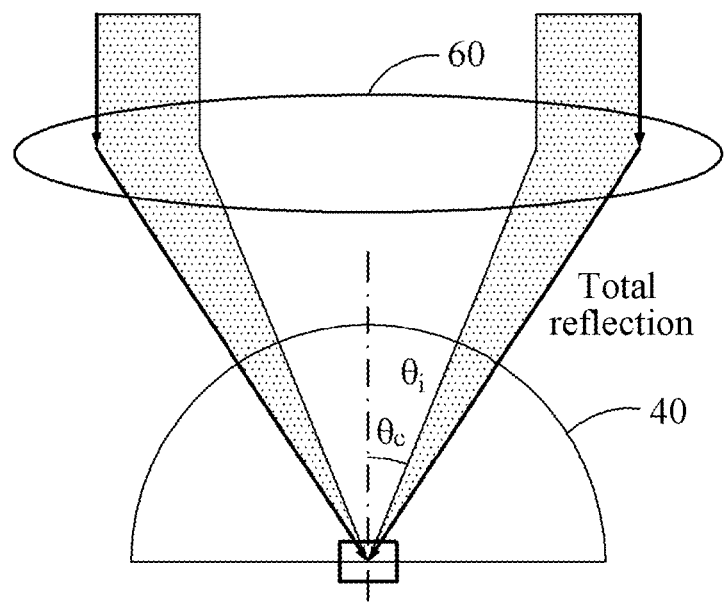
FIGS. 6A and 6B illustrate examples in which total internal reflection occurs on a bottom of a SIL of a fluorescence microscope according to at least some example embodiments.
Figure 6B:
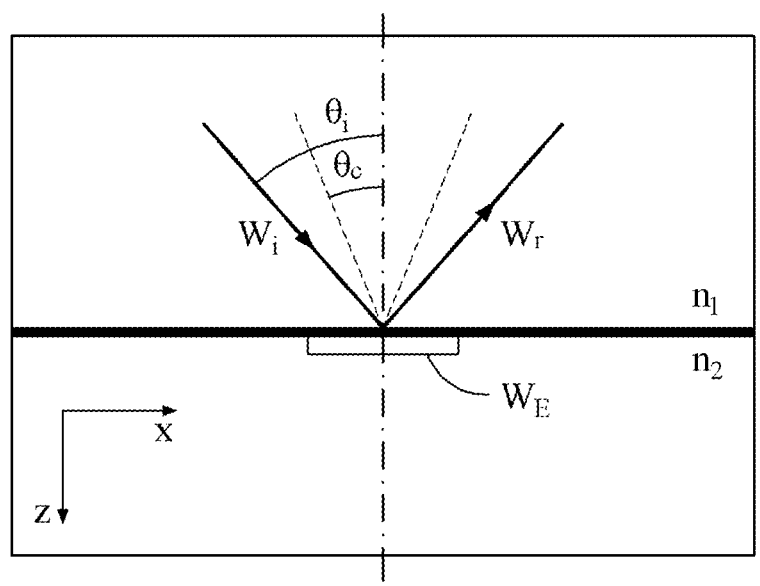

FIG. 4 illustrates an example of a fluorescence microscope according to at least one example embodiment, FIG. 5A illustrates an example of a path of excitation light incident from an object lens of a fluorescence microscope to a solid immersion lens (SIL) according to at least one example embodiment, FIG. 5B illustrates an example of a threshold angle of excitation light incident to a SIL of a fluorescence microscope according to at least one example embodiment, and FIGS. 6A and 6B illustrate examples in which total internal reflection occurs on a bottom of a SIL of a fluorescence microscope according to at least some example embodiments.

Referring to FIG. 4, FIGS. 5A and 5B, and FIGS. 6A and 6B, a fluorescence microscope 1 according to at least some example embodiments may include an excitation light source 10, a de-excitation light source 20, an optical body 30, a SIL 40, and an aperture 50.

The excitation light source 10 may emit excitation light that excites a fluorescent substance contained in a specimen S.

The de-excitation light source 20 may emit de-excitation light that de-excites the fluorescent substance excited by the excitation light emitted from the excitation light source 10.

If the excitation light emitted from the excitation light source 10 has a first wavelength, the de-excitation light emitted from the de-excitation light source 20 may have a second wavelength. The first wavelength may have a length less than the second wavelength.

A phase plate 21 may be provided in a path of the de-excitation light. The phase plate 21 may serve to form the de-excitation light in a donut shape.

When the excitation light source 10 and the de-excitation light source 20 are pulse lasers, a device for adjusting a pulse-width condition may be added. In the case of using a continuous wave (CW) laser, a beam expansion device and a collimation device for making beams in parallel may be added.

Also, although FIG. 4 illustrates that the excitation light source 10 is provided to be close to an object lens 60, locations of the excitation light source 10 and the de-excitation light source 20 may be exchanged with each other.

The optical body 30 may serve to overlap the excitation light emitted from the excitation light source 10 and the de-excitation light emitted from the de-excitation light source 20, and to discharge the overlapped light toward the specimen S.

The object lens 60 configured to refract the light discharged from the optical body 30 to be incident toward the SIL 40 may be provided between the optical body 30 and the SIL 40.

The optical body 30 may include an excitation light transmitter 31 configured to transfer the excitation light emitted from the excitation light source 10 toward the specimen S, and a de-excitation light transmitter 32 configured to transfer the de-excitation light emitted from the de-excitation light source 20.

The excitation light transmitter 31 and the de-excitation light transmitter 32 may be dichroic mirrors or beam splitters configured to reflect the excitation light or the de-excitation light, and to allow a fluorescent light emitted from the fluorescent substance of the specimen S to pass.

In more detail, the excitation light transmitter 31 and the de-excitation light transmitter 32 may be tilted at the respective preset angles, and may serve to reflect the excitation light and the de-excitation light toward the object lens 60, respectively, and may serve to allow the fluorescent light generated from the specimen S to pass and be incident to a detector 70.

The light discharged from the optical body 30 may be incident to the SIL 40. The SIL 40 may serve to refract the light discharged from the optical body 30 toward the specimen S. The light discharged from the optical body 30 may be in a form in which the excitation light and the de-excitation light are overlapped.

The light discharged from the optical body 30 and incident to the object lens 60 may be refracted and then incident to the SIL 40. A maximum incidence angle of light may be represented as $\theta_m$ as shown in FIG. 5A. Here, $\theta_m$ (m: Marginal ray) denotes an incidence angle of light refracted from an edge of light incident to the object lens 60.

Referring to FIG. 5B, the light incident from the object lens 60 to the SIL 40 may be divided into an area less than or equal to a threshold angle $\theta_c$ and an area greater than the threshold angle $\theta_c$. If the light is incident to the area less than or equal to the threshold angle $\theta_c$, the transmission of light may occur in a far-field area. In the far-field area, regular transmission may occur without generating an evanescent wave.

Also, if the light is incident to the area greater than the threshold angle $\theta_c$, the transmission of light may occur in a near-field area. In the near-field area, coupled transmission by generation of an evanescent wave may occur.

That is, referring to FIGS. 6A and 6B, if an incidence angle $\theta_i$, of light refracted at the object lens 60 and incident to the SIL 40 is incident to the area greater than the threshold angle $\theta_c$, total internal reflection occurs on a bottom of the SIL 40. By generating an evanescent wave $W_E$ in the near-field area generated by the total internal reflection, the fluorescent reaction of the fluorescent substance may be acquired. The detector 70 configured to collect the fluorescent reaction of the fluorescent substance may be further provided.

Figure 7A:
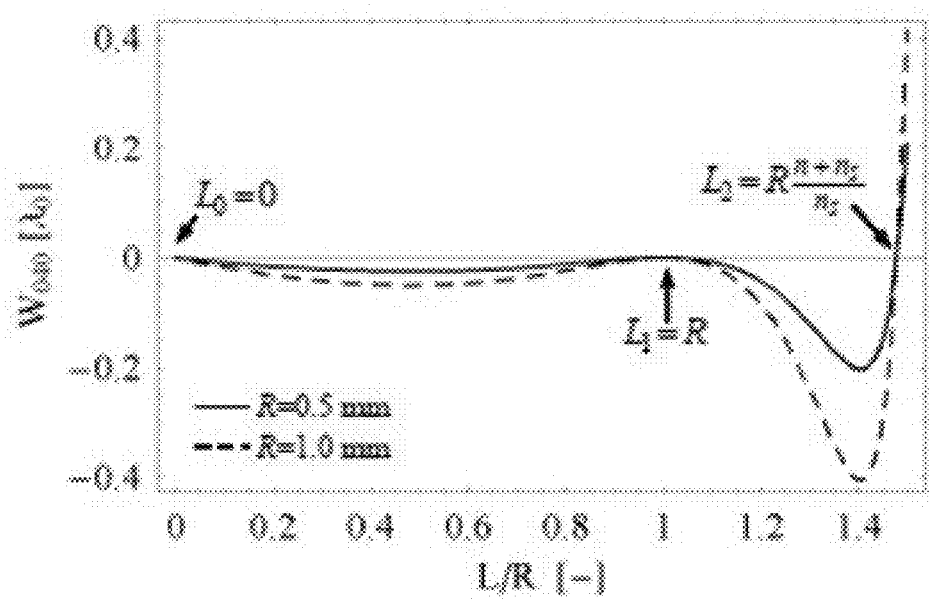
FIG. 7A is a graph showing an example of a spherical aberration of a SIL of a fluorescence microscope according to at least one example embodiment.
Figure 7B:
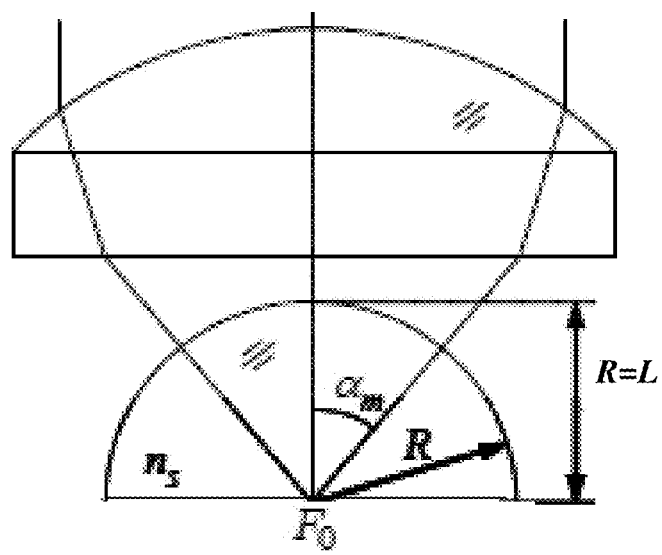
FIG. 7B illustrates an example in which a SIL of a fluorescence microscope is in a hemispherical shape according to at least one example embodiment.
Figure 7C:
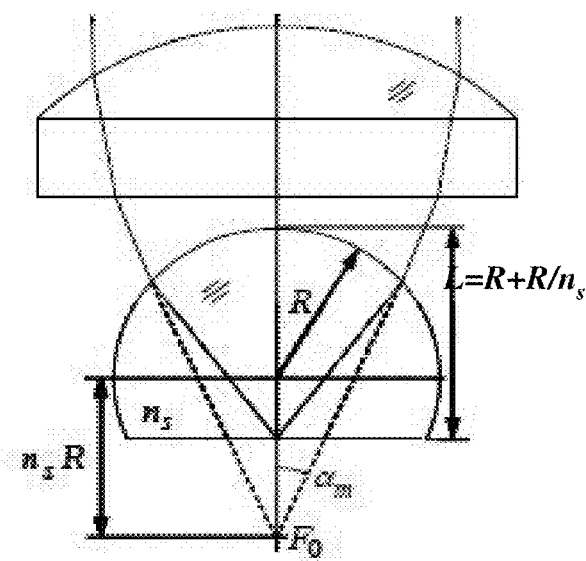
FIG. 7C illustrates an example in which a SIL of a fluorescence microscope is in a super-hemispherical shape according to at least one example embodiment.
Figure 8:
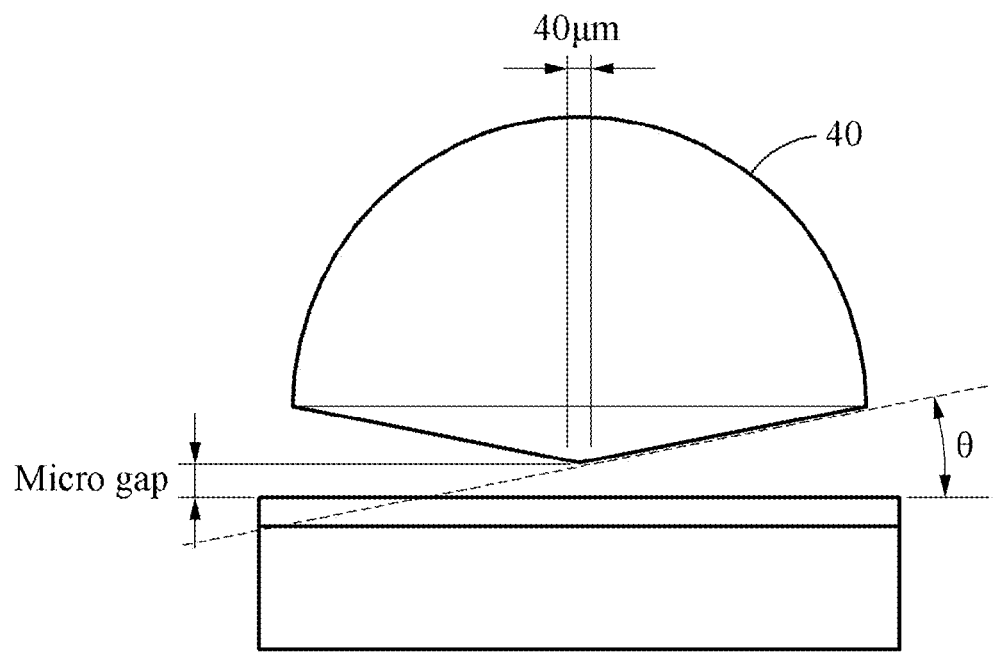
FIG. 8 illustrates an example of a bottom shape of a SIL of a fluorescence microscope according to at least one example embodiment.
Figure 9A:
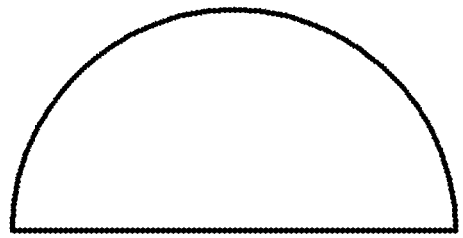
FIG. 9A illustrates an example in which a bottom of a SIL of a fluorescence microscope is processed to be as a plane surface according to at least one example embodiment.
Figure 9B:
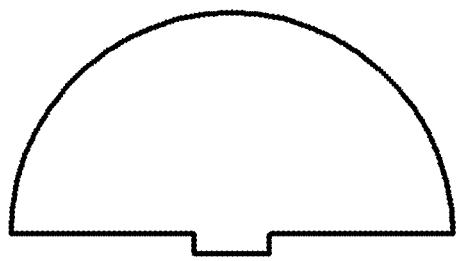
FIG. 9B illustrates an example in which a center of a bottom of a SIL of a fluorescence microscope is processed to be in a protruding shape according to at least one example embodiment.
Figure 9C:
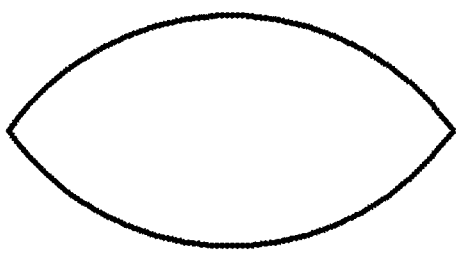
FIG. 9C illustrates an example in which a bottom of a SIL of a fluorescence microscope is processed to be in an oval shape according to at least one example embodiment.

FIG. 7A is a graph showing an example of a spherical aberration of a SIL of a fluorescence microscope according to at least one example embodiment, FIG. 7B illustrates an example in which a SIL of a fluorescence microscope is in a hemispherical shape according to at least one example embodiment, FIG. 7C illustrates an example in which a SIL of a fluorescence microscope is in a super-hemispherical shape according to at least one example embodiment, FIG. 8 illustrates an example of a bottom shape of a SIL of a fluorescence microscope according to at least one example embodiment, FIG. 9A illustrates an example in which a bottom of a SIL of a fluorescence microscope is processed to be as a plane surface according to at least one example embodiment, FIG. 9B illustrates an example in which a center of a bottom of a SIL of a fluorescence microscope is processed to be in a protruding shape according to at least one example embodiment, and FIG. 9C illustrates an example in which a bottom of a SIL of a fluorescence microscope is processed to be in an oval shape according to at least one example embodiment.

Referring to FIGS. 7A, 7B, 7C, FIG. 8, and FIGS. 9A, 9B, and 9C, the SIL 40 of the fluorescence microscope 1 according to at least some example embodiments may be provided in a hemispherical shape or a super-hemispherical shape that is a shape between a hemispherical shape and a spherical shape. Here, when the SIL 40 is in the spherical shape, it may be an optimal design. The shape of the SIL 40 is not limited thereto, and may be manufactured in a variety of shapes having a relatively low sensitivity over a thickness.

When the SIL 40 is in the hemispherical shape as shown in FIG. 7B, a radius R is equal to a length L from a focus $F_0$ (L=R). In this case, it can be verified from the graph of FIG. 7A that a spherical aberration (L/R) is smallest. Also, when the SIL is in the super-hemispherical shape as shown in FIG. 7C, it can be verified from the graph of FIG. 7A that the spherical aberration (L/R) is smallest if the radius R and the length L from the focus $F_0$ establish the relationship of $L=R+R/n_s$.

In the case of the SIL 40 manufactured in the spherical shape, the spherical aberration (L/R) may occur when light is focused on the bottom of the SIL 40. Thus, a thickness of the SIL 40 is to be accurately set. The hemispherical shape and the super-hemispherical shape have the smallest spherical aberration and thus, may be suitable for the shape of the SIL 40. Here, the super-hemispherical shape has a relatively high sensitivity over a thickness W of the SIL 40 and thus, may be further suitable for the shape of the SIL 40.

In the case of the SIL 40 in the hemispherical shape, if a light is refracted at the object lens 60 and is incident to the SIL 40, the light may be vertically incident on the surface of the SIL 40 and a numerical aperture (NA) may increase. Here, the NA may be represented by employing a refractive index and a maximum incidence angle as natural diffraction properties of light as expressed by Equation 1:

$$NA=n \sin \theta \quad (1)$$

A micro gap may be formed between the SIL 40 and the specimen S. A surface in parallel with the specimen S may be formed on a center of the bottom of the SIL 40. Also, referring to FIG. 8, an inclined surface may be formed on a peripheral portion excluding the center, to be away from the specimen S with getting closer from an inner peripheral portion toward an outer peripheral portion. For example, a diameter of the center may be about 40 µm and the micro gap may be about 5 to 20 nm.

In detail, the bottom of the SIL 40 may be processed so that a remaining peripheral portion excluding the center may be titled at a preset angle θ from the specimen S. For example, a maximum angle at which the SIL 40 and the specimen S maintain the micro gap of less than or equal to 20 nm may be less than or equal to 0.06 degrees as expressed by Equation 2.

$$\theta = \tan^{-1}[d/D_{SIL. \ tip}/2]] = \tan^{-1}(0.02/20) \leq \pm 0.06 \ deg. \quad (2)$$

Basically, the SIL 40 operates in a near field area. Thus, approach or contact is to be made so that a distance between the SIL 40 and the specimen S is tens of nm or less. Accordingly, the peripheral portion excluding the center of the bottom of the hemispherical shape that is the optimal shape for the SIL 40 may be processed in a conic shape and thereby used.

Here, the shape of the SIL 40 is not limited thereto and may be processed in a variety of shapes as shown in FIGS. 9A, 9B, and 9C.

Figure 10A:
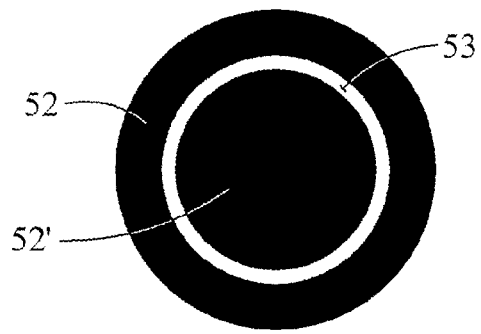
FIG. 10A is a cross-sectional view illustrating an example of an aperture of a fluorescence microscope according to at least one example embodiment.
Figure 10B:
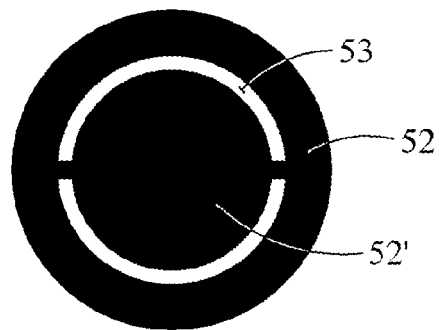
FIGS. 10B and 10C are cross-sectional views illustrating examples of other shapes of an aperture of a fluorescence microscope according to at least some example embodiments.
Figure 10C:
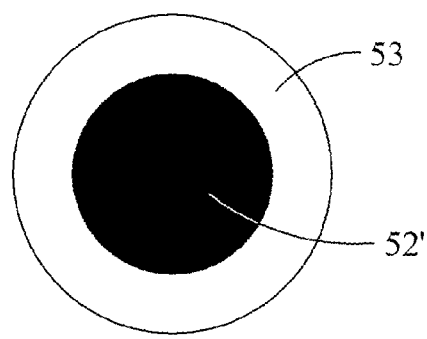
Figure 11A:
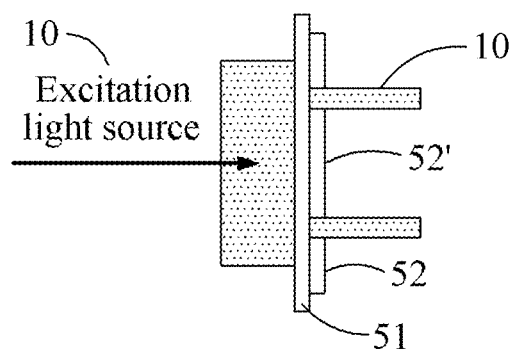
FIG. 11A is a side view illustrating an example in which light emitted from an excitation light source of a fluorescence microscope passes through an aperture according to at least one example embodiment.
Figure 11B:
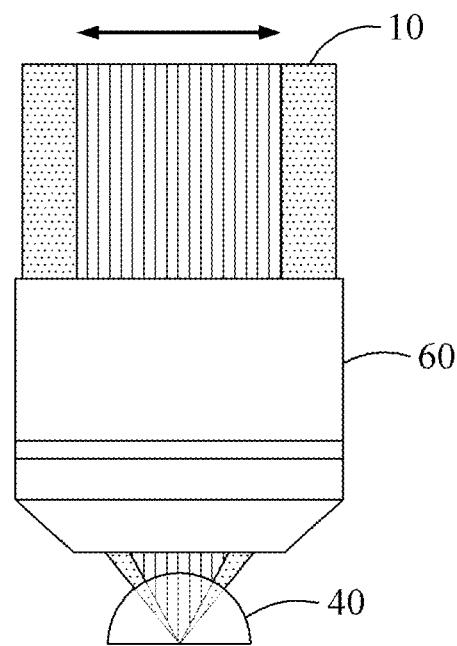
FIG. 11B is a cross-sectional view illustrating an example in which light emitted from an excitation light source of a fluorescence microscope is incident to an object lens according to at least one example embodiment.
Figure 12:
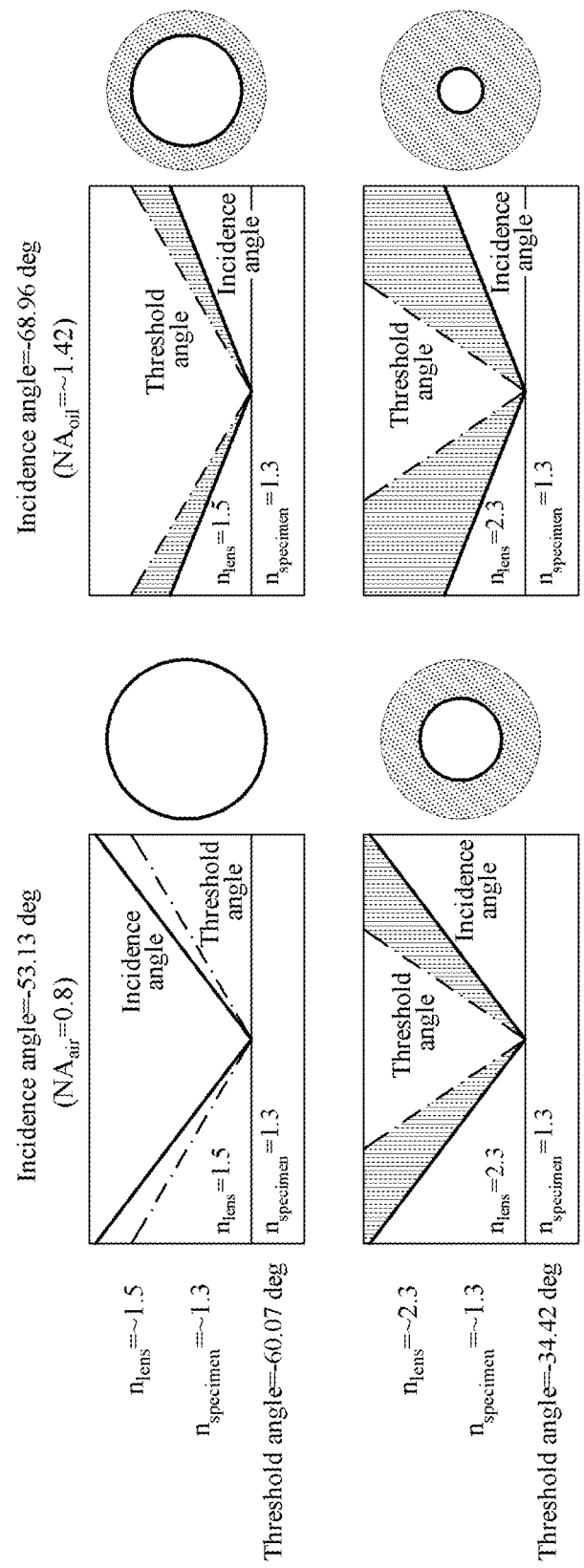
FIG. 12 illustrates examples of an increase in quantity of excitation light and a decrease in a threshold angle according to an increase in a numerical aperture (NA) of a fluorescence microscope according to at least some example embodiments.

FIG. 10A is a cross-sectional view illustrating an example of an aperture of a fluorescence microscope according to at least one example embodiment, FIGS. 10B and 10C are cross-sectional views illustrating examples of other shapes of an aperture of a fluorescence microscope according to at least some example embodiments, FIG. 11A is a side view illustrating an example in which light emitted from an excitation light source of a fluorescence microscope passes through an aperture according to at least one example embodiment, FIG. 11B is a cross-sectional view illustrating an example in which light emitted from an excitation light source of a fluorescence microscope is incident to the fluorescence microscope according to at least one example embodiment, and FIG. 12 illustrates examples of an increase in quantity of excitation light and a decrease in a threshold angle according to an increase in a NA of a fluorescence microscope according to at least some example embodiments.

Referring to FIGS. 10A, 10B, and 10C, FIGS. 11A and 11B, and FIG. 12, the fluorescence microscope 1 according to at least some example embodiments may include the aperture 50.

The aperture 50 may serve to adjust the distribution and quantity of light emitted from the excitation light source 10 by covering a portion of the excitation light source 10. Also, the aperture 50 may enable the light discharged from the optical body 30 to cause a total internal reflection to occur on the bottom of the SIL 40.

The aperture 50 may be used to block the center portion of the excitation light source 10. Also, the aperture 50 may be disposed at a location ahead of the excitation light transmitter 31 that reflects the excitation light source 10. That is, the aperture 50 may be disposed between the excitation light source 10 and the excitation light transmitter 31.

If the aperture 50 is disposed in front of the object lens 60, the de-excitation light source 20 is also blocked together and the intensity of radiation of de-excitation light for stimulated emission depletion (STED) may become weak. Accordingly, the aperture 50 may be disposed in front of the excitation light transmitter 31.

The aperture 50 may include a penetrator 51 formed of a transparent material and configured to allow the excitation light emitted from the excitation light source 10 to pass, and a shield 52 formed of an opaque material and configured to block the excitation light discharged from the excitation light source 10. In detail, by setting an incidence angle of excitation light incident to the SIL 40 to be greater than a threshold angle of excitation light based on an arrangement and an area of the penetrator 51 and the shield 52, 52', a total internal reflection may occur on the bottom of the SIL 40.

The penetrator 51 may be provided as a transparent plate to allow the excitation light to pass, and the shield 52, 52' may be provided as a black plate to block the excitation light. For example, the penetrator 51 and the shield 52, 52' may be provided as separate plates that are coupled to be separable. Also, the shield 52, 52' may be attached or painted on the penetrator 51 using a black tape, a black paint, etc.

Referring to FIG. 10A, a pass hole 53 in a ring shape may be formed on the shield 52, 52'. A remaining area excluding the pass hole 53 may serve to block the excitation light, and the excitation light may pass through the penetrator 51 and the pass hole 53 in the ring shape. Also, referring to FIG. 10B, in addition to the ring shape, the pass hole 53 may be provided in a ring shape of which at least a portion is cut. Without being limited thereto, the pass hole 53 may be formed in a variety of shapes within the range in which the incidence angle of excitation light is set to be greater than the threshold angle of excitation light.

That is, the aperture 50 may serve to block a light of an area corresponding to a threshold angle of excitation light or less in the light discharged from the optical body 30 and incident to the SIL 40.

Referring to FIGS. 11A and 11B, once the light emitted from the excitation light source 10 passes through the penetrator 51 and the shield 52, 52', a center portion of the excitation light may be blocked. Only excitation light having passed through the pass hole 53 in the ring shape may be incident to the object lens 60.

The light refracted at the object lens 60 and incident to the SIL 40 may be incident to the SIL 40 at an angle greater than the threshold angle. A total internal reflection may occur on the bottom of the SIL 40. For example, if a refractive index of the SIL 40 is $n_1$ and a refractive index of the specimen S is $n_2$, the refractive index $n_1$ of the SIL 40 may be greater than the refractive index $n_2$ of the specimen S to cause the total internal reflection to occur. An incidence angle of light incident to the SIL 40 may be greater than the threshold angle.

If the total internal reflection occurs on a boundary between the SIL 40 and the specimen S, an evanescent wave may occur at a relatively low refractive index. The evanescent wave is a progress direction of light present in the near field area, which is very short and of which intensity may decrease along an exponential function based on a progress distance. Accordingly, in the evanescent wave area, it is possible to locally observe the specimen S in which the fluorescent substance is painted. Thus, it is possible to observe a very thin portion, such as a cell membrane. Due to a very small transmission depth of the evanescent wave, it is possible to improve an image contrast compared to a general optical microscope.

Also, to cause the total internal reflection to occur between the SIL 40 and the specimen S, a NA indicating a light collection efficiency may be greater than a refractive index of specimen, that is, $n_{specimen}$.

An area less than or equal to $n_{specimen}$ in the entire NA area is an area less than the threshold angle. Thus, as shown in FIG. 12, light may be transmitted without generating the total internal reflection. For example, if a NA of a lens present in the air, i.e., $NA_{air}=0.8$ (an example in which the specimen is observed through the air using a lens with the NA of 0.8). If refractive index $n_{specimen}=1.3$, $NA_{air}<n_{specimen}$. Thus, the total internal reflection may not occur and the light transmission may occur.

Also, in the case of an oil, if $NA_{oil}=\sim 1.42$ and $n_{specimen}=1.3$, $NA_{oil}>N_{specimen}$. Thus, the light may be incident at the incidence angle greater than the threshold angle and the total internal reflection may occur.

In contrast, in the case of using the SIL 40, relatively high excitation intensity may be secured compared to an immersion lens using oil. Thus, it is possible to increase a resolution. For example, if $n_{lens}=\sim 2.3$ and $n_{specimen}=1.3$, the threshold angle may decrease compared to the immersion lens using oil. Thus, the intensity of radiation of incident excitation light may increase.

Figure 13A:
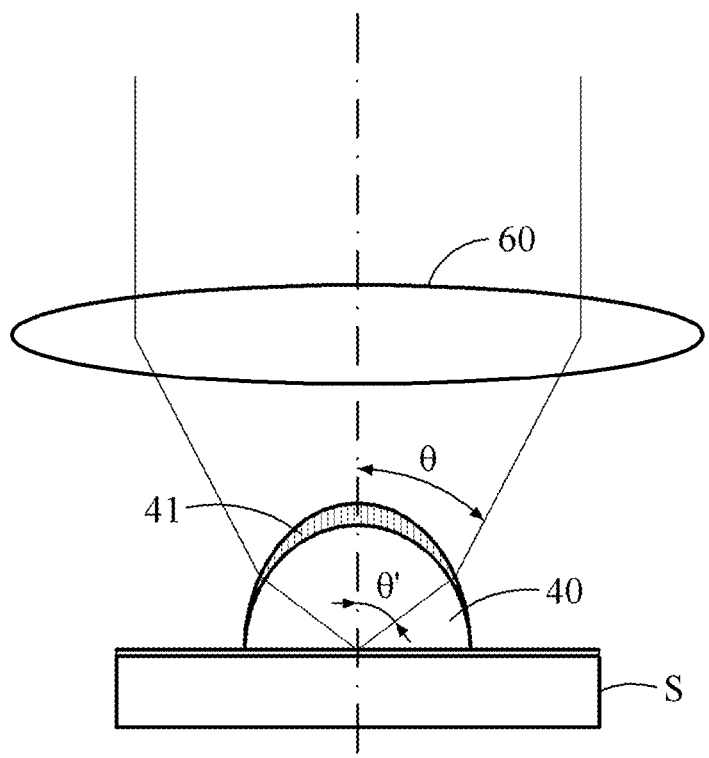
FIG. 13A illustrates an example in which a replicated immersion lens is provided on the surface of a SIL of a fluorescence microscope according to at least one example embodiment.
Figure 13B:
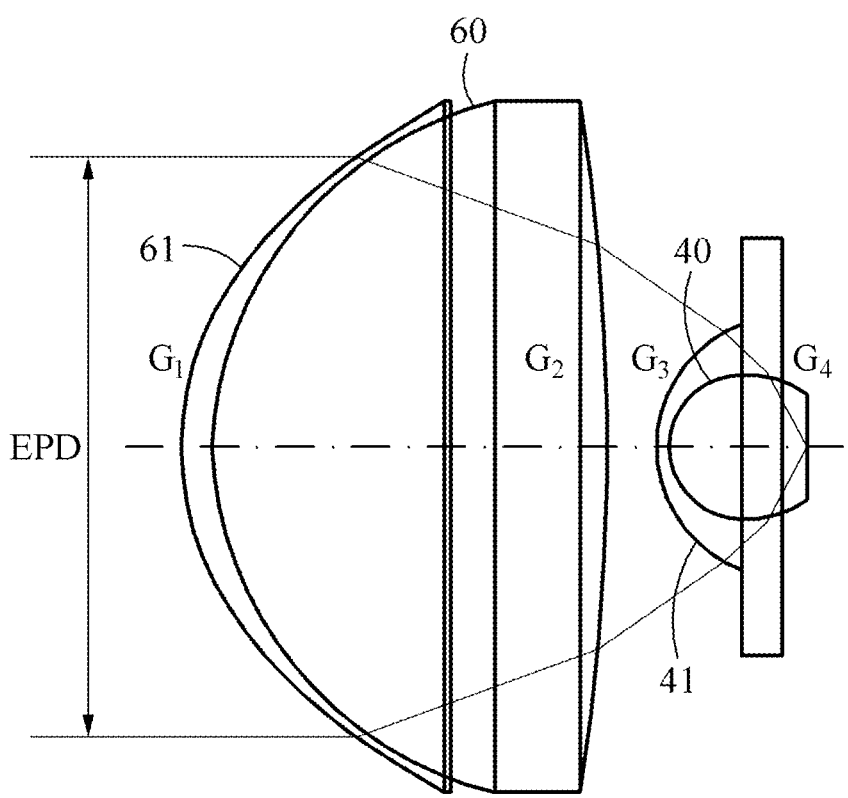
FIG. 13B illustrates an example in which a replicated immersion lens is provided to each of a SIL and a spherical object lens of a fluorescence microscope according to at least one example embodiment.

FIG. 13A illustrates an example in which a replicated immersion lens is provided on the surface of a SIL of a fluorescence microscope according to at least one example embodiment, and FIG. 13B illustrates an example in which a replicated immersion lens is provided to each of a SIL and a spherical object lens of a fluorescence microscope according to at least one example embodiment.

Referring to FIGS. 13A and 13B, a replicated immersion lens 41 may be provided on the surface of the SIL 40 of a fluorescence microscope according to at least one another example embodiment.

The replicated immersion lens 41 may be provided on the surface of the SIL 40, and may serve to increase a NA.

When the replicated immersion lens 41 is provided, light primarily refracted at the object lens 60 and thereby incident may be refracted once more at the replicated immersion lens 41. Thus, an incidence angle of the light incident to the SIL 40 may increase. For example, referring to FIG. 13A, if an incidence angle of light refracted at the object lens 60 and incident to the replicated immersion lens 41 is θ and an incidence angle of light refracted once more at the replicated immersion lens 41 and incident to the SIL 40 is θ', a relationship of θ<θ' may be established.

The replicated immersion lens 41 may serve to decrease the sensitivity over the thickness of the SIL 40 in the super-hemispherical shape.

In detail, referring to FIG. 13B, the first replicated immersion lens 41 may be provided on the surface of the SIL 40, and a second replicated immersion lens 61 may be provided on the surface of the object lens 60. The light discharged from the optical body 30 may be primarily incident to and refracted at the second replicated immersion lens 61 and then incident to the object lens 60. The incident light may be secondarily refracted at the object lens 60. The light discharged from the object lens 60 may be tertiarily refracted at the first replicated immersion lens 41 and incident to the SIL 40, and may be refracted at the SIL 40 as a final stage. In this manner, the total internal reflection may occur on the center of the bottom of the SIL 40.

Figure 14A:
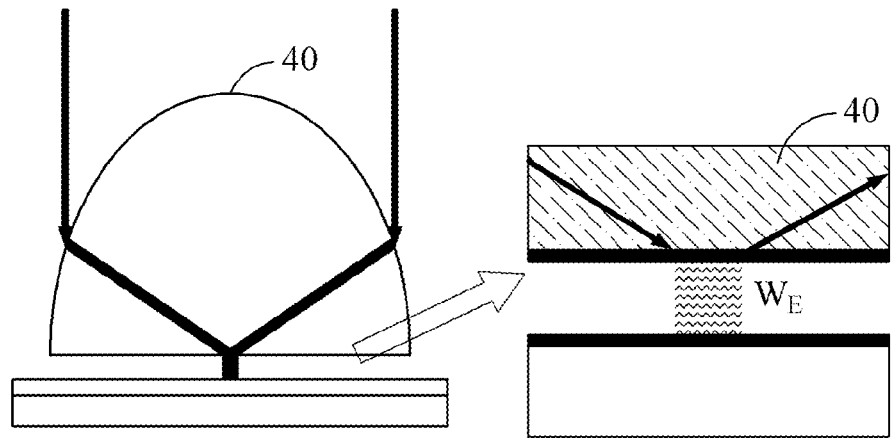
FIG. 14A illustrates an example in which a SIL of a fluorescence microscope is in an oval shape according to at least one example embodiment.
Figure 14B:
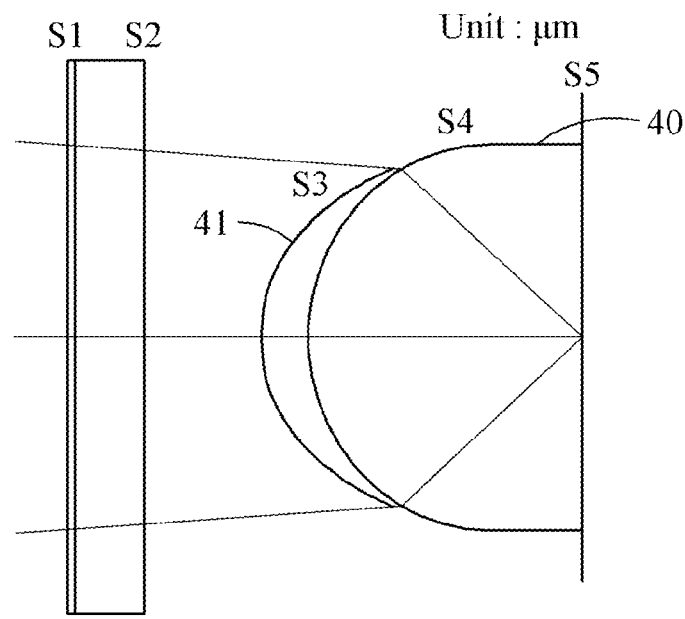
FIG. 14B illustrates an example in which a replicated immersion lens is provided on the surface of a SIL of a fluorescence microscope and a light is focused on a bottom of the SIL according to at least one example embodiment.

FIG. 14A illustrates an example in which a SIL of a fluorescence microscope is in an oval shape according to at least one example embodiment, and FIG. 14B illustrates an example in which a replicated immersion lens is provided on the surface of a SIL of a fluorescence microscope and a light is focused on a bottom of the SIL according to at least one example embodiment.

Referring to FIGS. 14A and 14B, the SIL 40 of the fluorescence microscope 1 may be provided in an oval shape.

If the SIL 40 is provided in the oval shape, the light discharged from the optical body 30 may be immediately incident to the SIL 40 although the object lens 60 is not separately provided. The replicated immersion lens 41 configured to refract the light discharged from the optical body 30 may be provided on the surface of the SL 40.

The replicated immersion lens 41 is additionally coupled on the surface of the SIL 40. The light discharged from the optical body 30 may be primarily refracted at the replicated immersion lens 41 and then incident to the SIL 40. The replicated immersion lens 41 may enable the light to be focused on the bottom of the SIL 40.

The total internal reflection of the incident light may occur on the bottom of the SIL 40. Accordingly, an evanescent wave $W_E$ may occur on a micro gap formed between the SIL 40 and the specimen S, thereby enhancing a vertical resolution.

For example, the SIL 40 may be formed using a material of LaSF35 (n=2.086), and the replicated immersion lens 41 may be formed using a material of acrylate (n=1.55) capable of blocking ultraviolet rays.

Figure 15A:
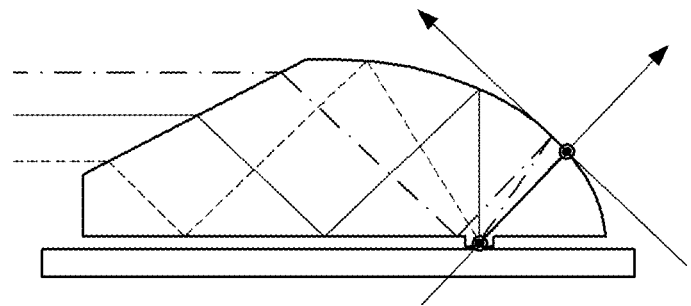
FIGS. 15A, 15B, and 15C illustrate examples in which a solid immersion mirror is provided instead of providing a SIL of a fluorescence microscope according to at least some example embodiments.
Figure 15B:
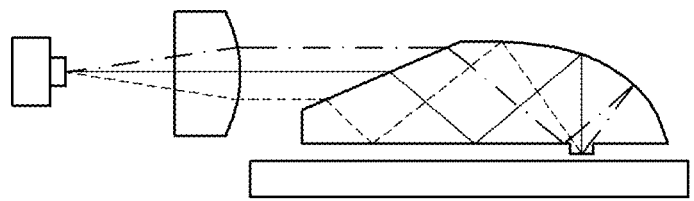
Figure 15C:
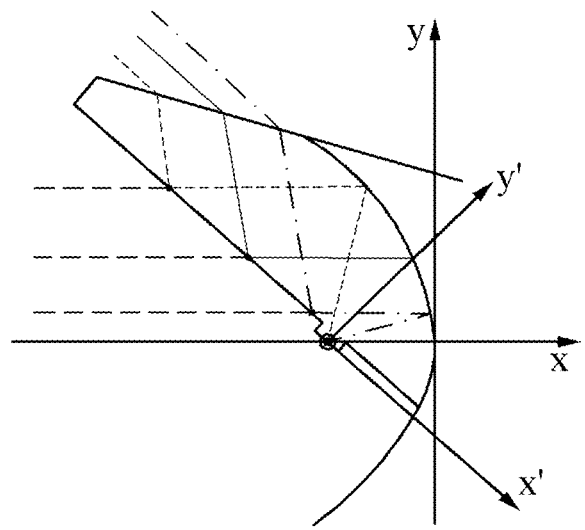

FIGS. 15A, 15B, and 15C illustrate examples in which a solid immersion mirror is provided instead of providing a SIL of a fluorescence microscope according to at least some example embodiments.

Referring to FIGS. 15A, 15B, and 15C, a fluorescence microscope according to at least one still another example embodiment may include a solid immersion mirror instead of the SIL 40.

The solid immersion mirror is not in a lens structure, which differs from the structure of the SIL 40. However, the similar effect may be achieved.

The sold immersion mirror may generate an evanescent wave through immersion using solid, which is the same as the SIL 40, and may acquire a fluorescent reaction of a fluorescent substance by total internal reflection.

That is, the light discharged from the optical body 30 may be separated into at least one light through a collimator lens and the separate light may be incident to the sold immersion mirror. The light incident to the sold immersion mirror may be reflected at a variety of angles, and may be focused on one side of the bottom of the solid immersion mirror.

A protrusion configured to focus the light incident to the solid immersion mirror may be provided on one side of the bottom of the solid immersion mirror. For example, the protrusion may be 5 μm. Also, the protrusion and the specimen S may be spaced apart from each other at a preset interval. Similar to the SIL 40, the solid immersion mirror may operate in a near field area. Thus, approach or contact may be made so that a distance between the specimen S and the bottom of the solid immersion mirror is tens of nm or less.

Figure 16A:
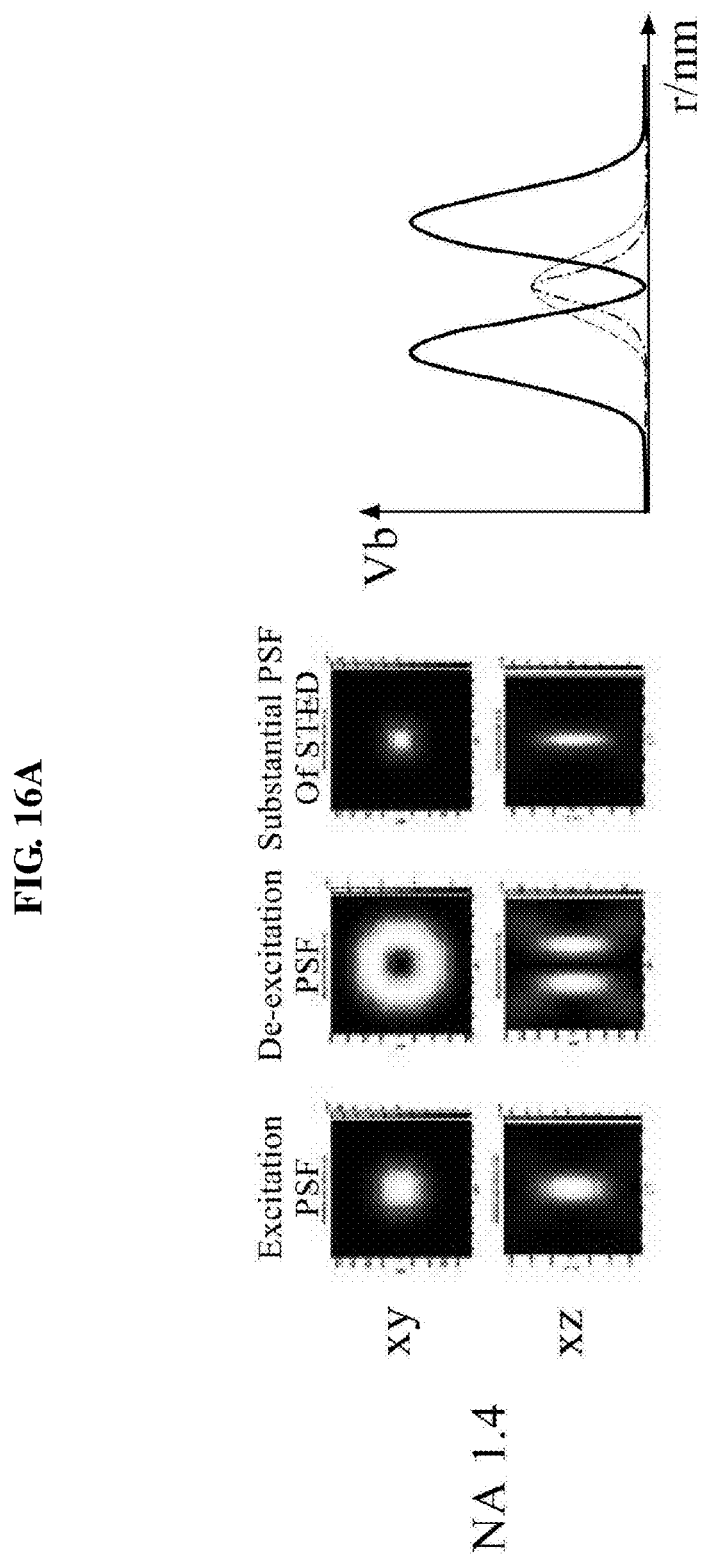
FIG. 16A illustrates an example of a point spread function (PSF) of excitation light by a STED phenomenon if a NA of a fluorescence microscope is 1.4 according to at least one example embodiment.
Figure 16B:
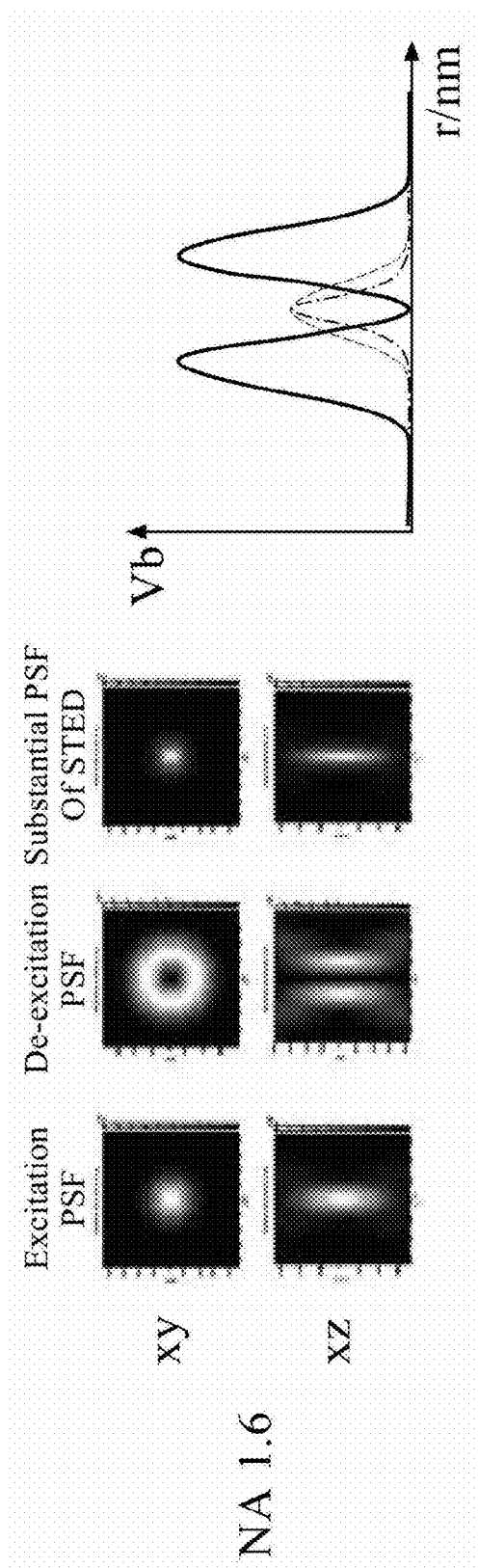
FIG. 16B illustrates an example of a PSF of excitation light by a STED phenomenon if a NA of a fluorescence microscope is 1.6 according to at least one example embodiment.
Figure 16C:
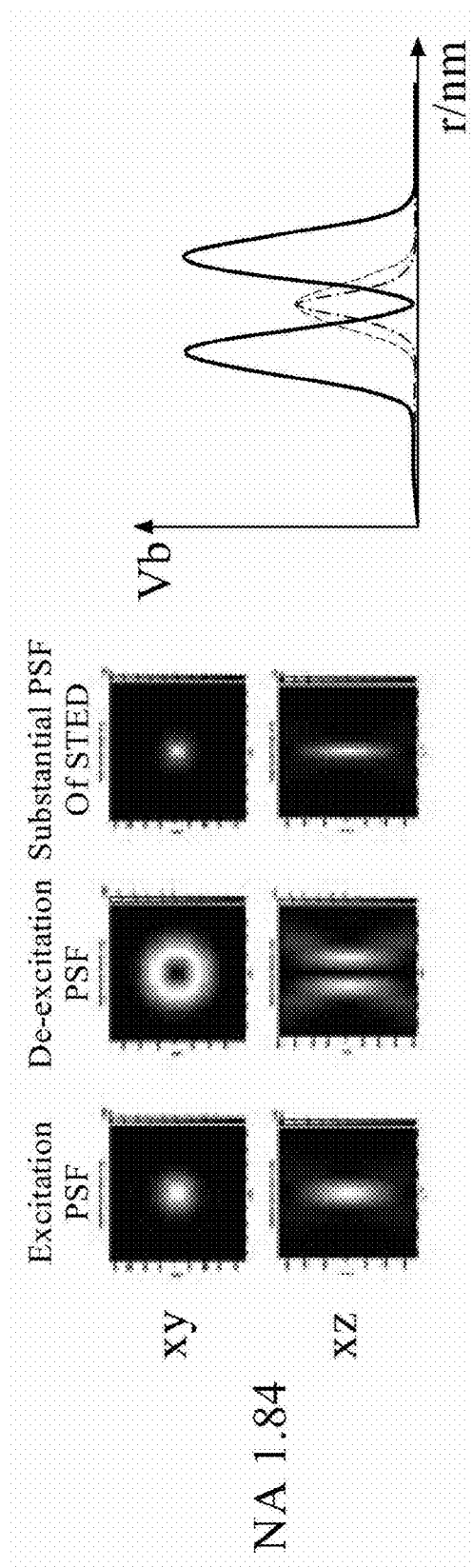
FIG. 16C illustrates an example of a PSF of excitation light by a STED phenomenon if a NA of a fluorescence microscope is 1.84 according to at least one example embodiment.
Figure 16D:
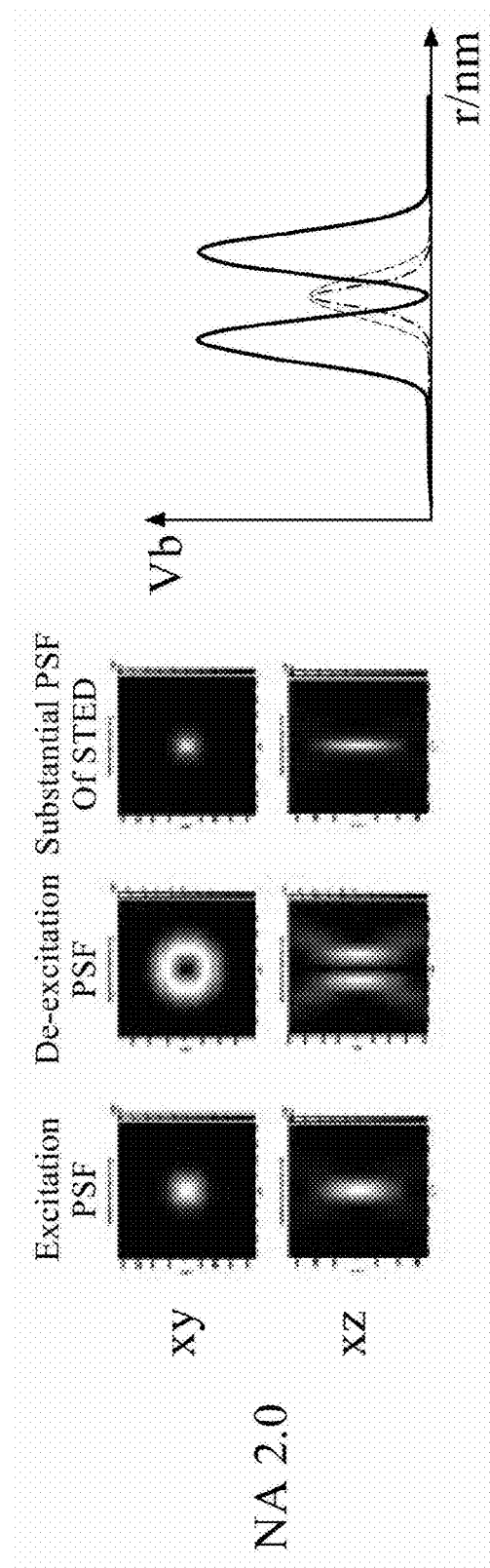
FIG. 16D illustrates an example of a PSF of excitation light by a STED phenomenon if a NA of a fluorescence microscope is 2.0 according to at least one example embodiment.

FIG. 16A illustrates an example of a point spread function (PSF) of excitation light by a STED phenomenon if a NA of a fluorescence microscope is 1.4 according to at least one example embodiment, FIG. 16B illustrates an example of a PSF of excitation light by a STED phenomenon if a NA of a fluorescence microscope is 1.6 according to at least one example embodiment, FIG. 16C illustrates an example of a PSF of excitation light by a STED phenomenon if a NA of a fluorescence microscope is 1.84 according to at least one example embodiment, and FIG. 16D illustrates an example of a PSF of excitation light by a STED phenomenon if a NA of a fluorescence microscope is 2.0 according to at least one example embodiment.

Referring to FIGS. 16A, 16B, 16C, and 16D, in a fluorescence microscope according to at least one example embodiment, a PSF of excitation light may vary based on a NA value.

De-excitation light incident toward the SIL 40 may generate a STED phenomenon that blocks and depletes a first wavelength of excitation light exciting a fluorescent substance in a neighboring area excluding a central area overlapping the excitation light, thereby increasing a horizontal resolution.

In detail, stimulated emission refers to a phenomenon that light of specific wavelength is incident to electrons transited to an excited state by absorbing energy and a characteristic of the incident light is replicated, thereby generating irradiation. The STED phenomenon may cause the stimulated emission by applying the stimulated emission phenomenon and by allowing de-excitation light to be incident to an edge portion of an excited fluorescent substance, and may increase a resolution by blocking the wavelength thereof.

Due to the STED phenomenon, an emission area of excitation light at a focusing location of light may be minimized. Thus, an image with a further enhanced horizontal resolution may be acquired. A resolution and efficiency by the STED phenomenon may be expressed as shown in Equation 3.

$$\text{Full width at half maximum}(FWHM) = \frac{\lambda_{ex}}{\alpha NA\sqrt{1 + \beta I_{dep}/I_s}} \quad (3)$$

$I_s$: Saturation intensity, $I_{dep}$: Intensity of de-excitation light source

Compared to an oil immersion lens according to the related art, the fluorescence microscope 1 according to at least some example embodiments may secure a relatively high NA using the SIL 40. Hereinafter, results of translating an increase in a resolution based on a NA will be described. Here, as the translation conditions, only a NA was changed and all of an excitation wavelength, a de-excitation wavelength, and intensity of each wavelength at a focus were set to be the same. Here, wavelength=635 nm, de-excitation wavelength=780 nm, excitation intensity at focus=1 MW/mm², and de-excitation intensity at focus=10 MW/mm².

For example, referring to FIGS. 16A, 16B, 16C, and 16D, changes may be made based on NA=1.4, 1.6, 1.84, and 2.0. Compared to a case of NA=1.4, if NA=2.0, a substantial PSF by stimulated emission depletion is further excellent.

That is, it can be verified that a substantial PSF appearing when overlapping an excitation PSF by the excitation light source 10 and a de-excitation PSF by the de-excitation light source 20 has an enhanced resolution according to an increase in a NA value.

Figure 17:
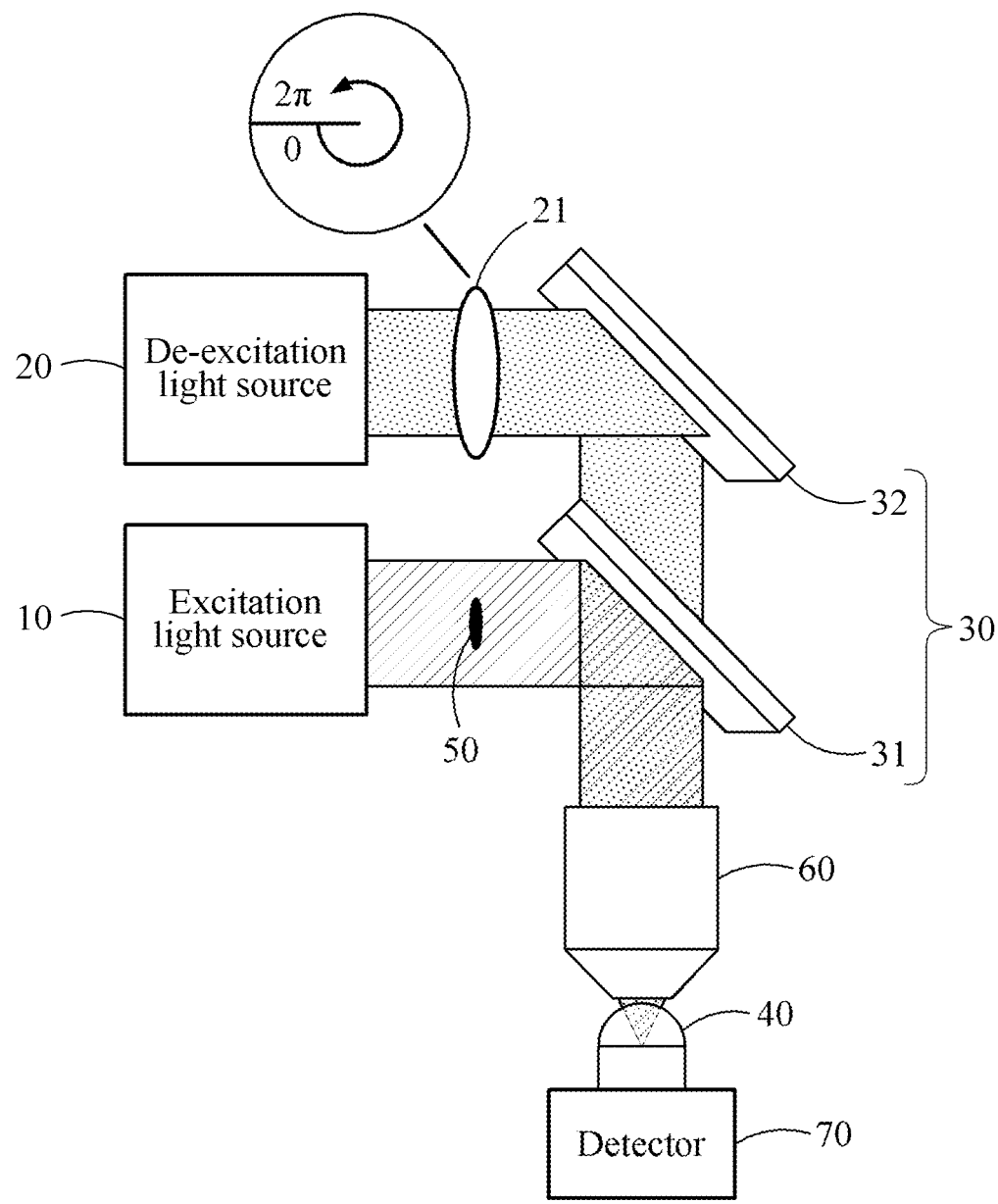
FIG. 17 illustrates an example in which a detector of a fluorescence microscope is provided to face a SIL according to at least one example embodiment.

FIG. 17 illustrates an example in which a detector of a fluorescence microscope is provided to face a SIL according to at least one example embodiment.

Referring to FIG. 17, the detector 70 of the object lens 60 according to at least one example embodiment may be provided to face the SIL 40.

Depending on example embodiments, the detector 70 may be provided above the object lens 60, below the object lens 60, between the excitation light transmitter 31 and the de-excitation light transmitter 32 and the object lens 60, or between the excitation light transmitter 31 and the de-excitation light transmitter 32.

For example, if the detector 70 is provided to face the object lens 60, that is, if the detector 70 is provided below the object lens 60, an optical device to collect the fluorescent reaction of fluorescent substance may be further provided to face the SIL 40.

Hereinafter, an operation of a fluorescence microscope according to at least some example embodiments will be described.

The fluorescence microscope 1 may employ a structure that includes the SIL 40 in order to increase a NA.

The excitation light emitted from the excitation light source 10 and the light emitted from the de-excitation light source 20 may be reflected through the optical body 30, and may be incident to the object lens 60. The light refracted at the object lens 60 may be incident to the SIL 40 in the hemispherical shape, and may be incident to be vertical on the surface of the SIL 40. In this manner, the NA may increase.

Here, since an incidence angle may exceed a threshold angle in an outer portion of light incident to the SIL 40, a total internal reflection may occur and an evanescent wave $W_E$ may be generated on the bottom of the SIL 40. By blocking a low NA area, for example, an area within the threshold angle, of light incident to the SIL 40 using the aperture 50, it is possible to configure a total internal reflection fluorescence microscope (TIRFM) structure based on the evanescent wave $W_E$.

In particular, the aperture 50 may serve to adjust a transmission area of excitation light incident to the object lens 60, and thereby make the excitation light incident to the SIL 40 at a threshold angle or more.

In the case of increasing a NA using the SIL 40, it is possible to increase a resolution of an acquired image in both a horizontal direction and a vertical direction. Also, it is possible to further increase a horizontal resolution by adding STED technology.

Accordingly, it is possible to acquire an optical image of which resolution has overcome a diffraction limited performance in both the horizontal direction and the vertical direction of the specimen S including the fluorescent substance.

Although a few example embodiments have been shown and described, the present disclosure is not limited to the described embodiments. Instead, it would be appreciated by those skilled in the art that changes may be made to these embodiments without departing from the principles and spirit of the disclosure, the scope of which is defined by the claims and their equivalents.

What is claimed is:

1. A total internal reflection fluorescence microscope (TIRFM) for imaging a specimen containing a fluorescent substance, the TIRFM comprising:
   an excitation light source configured to emit an excitation light that excites the fluorescent substance to emit fluorescence;
   a de-excitation light source configured to emit a de-excitation light that de-excites the fluorescent substance excited by the excitation light emitted from the excitation light source;
   an optical body configured to overlap a light emitted from the excitation light source and a light emitted from the de-excitation light source, and to discharge the overlapped light toward the specimen; and
   a solid immersion lens to which the light discharged from the optical body is incident, and configured to refract the light discharged from the optical body toward the specimen,
   wherein a total internal reflection of the light incident to the solid immersion lens occurs on a bottom of the solid immersion lens.

2. The TIRFM of claim 1, further comprising:
   an aperture configured to cover a portion of the excitation light emitted from the excitation light source.

3. The TIRFM of claim 2, wherein the aperture is configured to block a light of an area on which a total internal reflection does not occur on the bottom of the solid immersion lens in the excitation light incident to the solid immersion light by blocking a portion of the excitation light emitted from the excitation light source.

4. The TIRFM of claim 3, wherein the aperture is configured to block a light of an area corresponding to a threshold angle or less in the excitation light incident to the solid immersion light by blocking a portion of the excitation light emitted from the excitation light source.

5. The TIRFM of claim 2, wherein the aperture comprises:
   a penetrator formed of a transparent material, and configured to allow the excitation light emitted from the excitation light source to pass; and
   a shield formed of an opaque material, and configured to block the excitation light discharged from the excitation light source, and the penetrator and the shield are provided so that an incidence angle of the excitation light incident to the solid immersion lens is greater than a threshold angle.

6. The TIRFM of claim 5, wherein the shield is provided in a circular shape to block a center of the excitation light emitted from the excitation light source, and the penetrator is provided in a ring shape around the shield.

7. The TIRFM of claim 1, further comprising:
   a detector configured to detect a fluorescent light from the fluorescent substance of the specimen.

8. The TIRFM of claim 1, wherein the optical body comprises:
   an excitation light transmitter configured to transfer the excitation light emitted from the excitation light source toward the specimen; and
   a de-excitation light transmitter configured to transfer the de-excitation light emitted from the de-excitation light source toward the specimen.

9. The TIRFM of claim 8, wherein the excitation light transmitter and the de-excitation light transmitter are dichroic mirrors or beam splitters configured to reflect the excitation light or the de-excitation light, and to allow a fluorescent light emitted from the fluorescent substance of the specimen to pass.

10. The TIRFM of claim 1, wherein an object lens configured to allow the light discharged from the optical body to be incident toward the solid immersion lens is provided below the optical body.

11. The TIRFM of claim 1, wherein, in response to the excitation light being incident to the solid immersion lens at an angle greater than a threshold angle, a total internal reflection occurs on the bottom of the solid immersion lens, an evanescent wave toward the specimen occurs on the solid immersion lens, and a fluorescent light of the fluorescent substance generated by the evanescent wave is detected.

12. The TIRFM of claim 1, wherein pieces of the de-excitation light are formed in a donut shape to overlap the excitation light on a neighboring area excluding a central area of the excitation light, and
   a horizontal resolution increases in response to an occurrence of a simulated emission depletion (STED) phenomenon that de-excites the excitation light for exciting the fluorescent substance.

13. The TIRFM of claim 10, wherein the solid immersion lens is provided in a hemispherical shape, and the light discharged from the object lens is incident to be vertical to the surface of the solid immersion lens and to increase a light collecting efficiency.

14. The TIRFM of claim 13, further comprising:
   a replicated lens configured to refract the light discharged from the optical body on the surface of the solid immersion lens or the object lens.

15. The TIRFM of claim 13, wherein the bottom of the solid immersion lens is provided in a conic shape that is upwardly inclined with getting closer from a center to an edge.

16. A total internal reflection fluorescence microscope (TIRFM) for imaging a specimen containing a fluorescent substance, the TIRFM comprising:
   an excitation light source configured to emit a first wavelength of an excitation light that excites the fluorescent substance;
   a de-excitation light source configured to emit a second wavelength of a de-excitation light that de-excites the fluorescent substance excited by the excitation light emitted from the excitation light source;

an optical body configured to overlap a light emitted from the excitation light source and a light emitted from the de-excitation light source, and to discharge the overlapped light toward the specimen;

a solid immersion lens to which the light discharged from the optical body is incident, and configured to refract the light discharged from the optical body toward the specimen;

an aperture configured to adjust an amount of light emitted from the excitation light source by covering at least a portion of the excitation light source and to enable the light discharged from the optical body to cause a total internal reflection on a bottom of the solid immersion lens; and a detector configured to collect a fluorescent reaction of the fluorescent substance that has received the light discharged from the optical body.

17. The TIRFM of claim 16, wherein the aperture is configured to block a light of an area on which the total internal reflection does not occur on the bottom of the solid immersion lens in the excitation light incident to the solid immersion lens by blocking a portion of the excitation light emitted from the excitation light source.

18. The TIRFM of claim 17, wherein the aperture is configured to block a light of an area corresponding to a threshold angle or less in the excitation light incident to the solid immersion light by blocking a portion of the excitation light emitted from the excitation light source.

19. The TIRFM of claim 16, wherein the aperture comprises:

a penetrator formed of a transparent material, and configured to allow the excitation light emitted from the excitation light source to pass; and a shield formed of an opaque material, and configured to block the excitation light discharged from the excitation light source, and the penetrator and the shield are provided so that an incidence angle of the excitation light incident to the solid immersion lens is greater than a threshold angle.

20. The TIRFM of claim 16, wherein the shield is provided in a circular shape to block a center of the excitation light emitted from the excitation light source, and the penetrator is provided in a ring shape around the shield.

* * * * *